(12) United States Patent
Lohier et al.

(10) Patent No.: US 10,905,309 B2
(45) Date of Patent: Feb. 2, 2021

(54) METHOD AND APPARATUS FOR ENFORCED PROVISIONING AND COMPLIANT USAGE AUTHORIZATION OF ENDOSCOPE APPLICATIONS

(71) Applicant: REED CAM, INC., Castro Valley, CA (US)

(72) Inventors: Frantz Roger Lohier, El Cerrito, CA (US); Ali Alex Moayer, Castro Valley, CA (US)

(73) Assignee: REED CAM, INC., Castro Valley, CA (US)

( * ) Notice: Subject to any disclaimer, the term of this patent is extended or adjusted under 35 U.S.C. 154(b) by 30 days.

(21) Appl. No.: 16/358,678

(22) Filed: Mar. 19, 2019

(65) Prior Publication Data

US 2020/0297183 A1  Sep. 24, 2020

(51) Int. Cl.
*A61B 1/00* (2006.01)
*G16H 40/63* (2018.01)
*A61B 1/045* (2006.01)

(52) U.S. Cl.
CPC ........ *A61B 1/00006* (2013.01); *A61B 1/0002* (2013.01); *A61B 1/00059* (2013.01); *A61B 1/00103* (2013.01); *A61B 1/00124* (2013.01); *A61B 1/00128* (2013.01); *A61B 1/045* (2013.01); *G16H 40/63* (2018.01)

(58) Field of Classification Search
CPC . A61B 1/00006; A61B 1/00059; A61B 1/045; A61B 1/00103; A61B 1/0002; A61B 1/00124; A61B 1/00128; A61B 1/00062; G16H 40/63
See application file for complete search history.

(56) References Cited

U.S. PATENT DOCUMENTS

| | | | | |
|---|---|---|---|---|
| 2003/0009083 A1* | 1/2003 | Takahashi | .......... | A61B 1/00059 600/109 |
| 2004/0024290 A1* | 2/2004 | Root | .................. | A61B 1/00062 600/160 |
| 2004/0186382 A1* | 9/2004 | Modell | ................ | A61B 5/0075 600/473 |
| 2004/0236606 A1* | 11/2004 | Oishi | ..................... | G16H 40/20 705/2 |
| 2005/0261551 A1* | 11/2005 | Couvillon, Jr. | .... | A61B 1/00105 600/118 |
| 2006/0183972 A1* | 8/2006 | Tashiro | .............. | A61B 1/00041 600/101 |

(Continued)

*Primary Examiner* — Ryan W Sherwin
(74) *Attorney, Agent, or Firm* — Winston Hsu

(57) ABSTRACT

An endoscope apparatus capable of ensuring safe and compliant use includes an endoscope, a means for identification of the endoscope, a means for determining whether the endoscope is suitable for a given medical act utilizing the identification of the endoscope, and a disablement means that prevents utilization of the endoscope when determined the endoscope is not suitable for the given medical act. The identification may be on a tag fixed to the endoscope and/or container. The information is checked for a match in a cloud database to ensure the endoscope is the right device for the medical act. If not the right device, the endoscope is deactivated. If the right device, the endoscope is activated and the cloud database is updated accordingly. The cloud database can also be updated at each point in the distribution chain to allow complete traceability.

21 Claims, 3 Drawing Sheets

(56) References Cited

U.S. PATENT DOCUMENTS

| | | | | |
|---|---|---|---|---|
| 2007/0273759 A1* | 11/2007 | Krupnick | .............. | H04N 5/225 |
| | | | | 348/45 |
| 2008/0091065 A1* | 4/2008 | Oshima | ................ | H04N 19/60 |
| | | | | 600/109 |
| 2008/0162184 A1* | 7/2008 | Matsubara | ............ | G16H 40/63 |
| | | | | 705/2 |
| 2009/0065034 A1* | 3/2009 | Suzuki | ...................... | A61L 2/18 |
| | | | | 134/56 R |
| 2009/0103836 A1* | 4/2009 | Shimizu | ................ | A61B 90/70 |
| | | | | 382/305 |
| 2010/0071736 A1* | 3/2010 | Watanabe | .......... | A61B 1/00006 |
| | | | | 134/56 R |
| 2010/0249508 A1* | 9/2010 | Sato | ...................... | A61B 1/041 |
| | | | | 600/117 |
| 2012/0071710 A1* | 3/2012 | Gazdzinski | .......... | A61B 1/0002 |
| | | | | 600/101 |
| 2013/0137377 A1* | 5/2013 | Endo | ................. | A61B 1/00059 |
| | | | | 455/66.1 |
| 2013/0300829 A1* | 11/2013 | Urasaki | .............. | A61B 1/00009 |
| | | | | 348/45 |
| 2014/0118517 A1* | 5/2014 | Fueki | .................... | G16H 70/60 |
| | | | | 348/65 |
| 2014/0118518 A1* | 5/2014 | Fructus | .............. | A61B 1/00059 |
| | | | | 348/65 |
| 2017/0034437 A1* | 2/2017 | Kutsuma | ................... | G06T 5/00 |
| 2019/0206562 A1* | 7/2019 | Shelton, IV | ........... | B25J 13/006 |
| 2019/0246873 A1* | 8/2019 | Lu | ...................... | A61B 1/00144 |
| 2020/0100655 A1* | 4/2020 | Morishima | ............ | A61B 1/053 |

\* cited by examiner

METHOD AND APPARATUS FOR ENFORCED PROVISIONING AND COMPLIANT USAGE AUTHORIZATION OF ENDOSCOPE APPLICATIONS

BACKGROUND OF THE INVENTION

1. Field of the Invention

The present disclosure describes a set of techniques to enforce the provisioning and authorization of medical endoscope instruments with a particular emphasis on endoscope designs restricted to one-time or limited use (or activation counts).

2. Description of the Prior Art

A main purpose of limited use endoscopes is to reduce cost and increase patient safety by limiting the use of endoscope parts that may be exposed to organic tissues. This notably simplifies sterilization and reduces contagion risks. Yet, limited mechanisms exist for such instruments to ensure provisioning and activation of only the right instrument using the right software for the right medical act.

SUMMARY OF THE INVENTION

An objective of the present invention is to provide a medical apparatus with disposable parts and associated software that ensure activation of only the right instrument for the right medical act. These goals are achieved via two mains steps; first, the device and or its storage container is provisioned with a set of settings during manufacturing time. Second, an authorization software is used prior to a medical exam to ensure that a given disposable endoscope solution (container and/or the endoscope device) is being used according to its operating limits and the intended exam goals and adds and/or limits software and cloud services.

These and other objectives of the present invention will no doubt become obvious to those of ordinary skill in the art after reading the following detailed description of the preferred embodiment that is illustrated in the various figures and drawings.

DETAILED DESCRIPTION

A detailed description of examples of preferred embodiments is provided below. While several embodiments are described, it should be understood that the new subject matter described in the present specification is not limited to any one embodiment or combination of embodiments described herein, but instead encompasses numerous alternatives.

A new class of disposable medical imaging endoscopes is emerging enabling practitioners to conduct safer and more compliant exams. Safer exams can be made possible thanks to the fact that such systems do not need to be sterilized for example (or only need to be partially sterilized), or that it is possible to detect that a unit was previously used and should not be reused. In addition, exams that are more compliant are possible by the fact that these new systems can be designed to enforce compliant usage by additionally determining when a unit should not be used for other reasons, for example, expiration of the unit, recall of the unit, invalid authorization software's license, and/or improper unit for a given medical procedure.

Limited use endoscopes offer numerous benefits over traditional reusable endoscope equipment including and not limited to cost, ease-of-use, size, patient comfort-level and simplified sterilization process. Ensuring the safe and compliant use of this new generation of devices is however largely dependent on ensuring that the disposable parts of such apparatus are used within its operating limits. These limits include confirming adequacy of certain detachable parts of the apparatus towards a given medical act, limiting or suppressing reuse for certain critical part(s) of the disposable endoscope apparatus, blocking improper use for certain critical part(s) of the disposable endoscope apparatus, and ensuring that sterilized packaging is traceable as part of the distribution chain of disposable endoscope parts.

Figure 1:
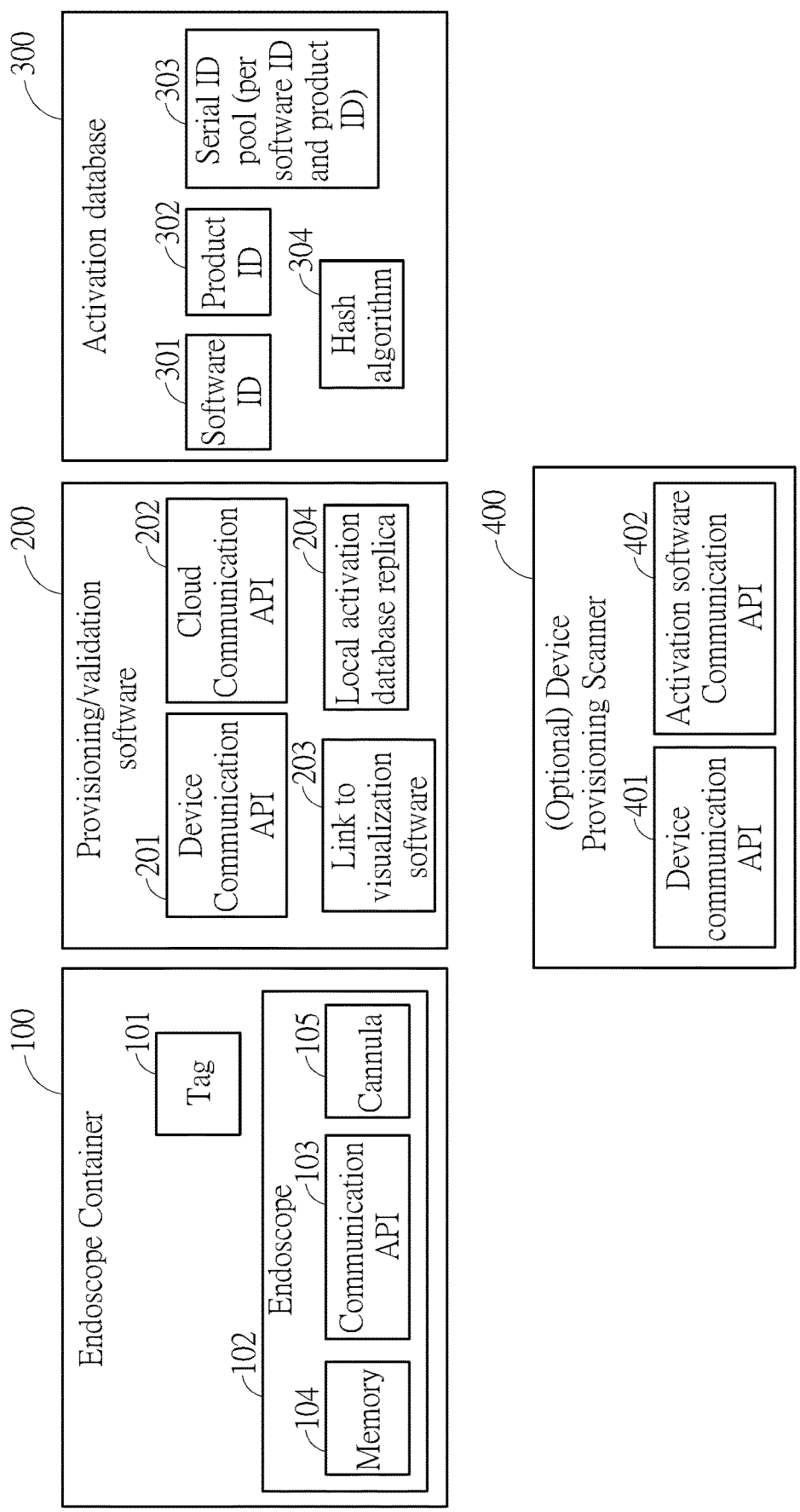
FIG. 1 illustrates a functional block diagram of an endoscope solution with device apparatus 102 with enforced provisioning, activation and/or compliance according to an embodiment of the invention.

FIG. 1 illustrates a functional block diagram of an endoscope apparatus 102 with enforced provisioning, authorization according to an embodiment of the invention. The endoscope apparatus 102 includes an endoscope container 100. The endoscope container 100 comprises a tag 101, and an endoscope device 102. The endoscope 102 comprises a communication application programming interface (API) 103 and a non-volatile memory 104. The non-volatile memory 104 preferably includes a form of non-volatile read-only memory (ROM) such as, inter alia, programmable read-only memory (PROM) or field programmable read-only memory (FPROM), or one-time programmable non-volatile memory.

Information about and/or identifying the Endoscope device can be stored both on the container (via some form of tag 101) and/or in the device's memory 104 or via a tag 101 directly attached to the endoscope device. This allows for 2 levels of validation prior to device activation. If only the container is validated by the validation software, then multiple devices could be used with the same container tag. On the other hand, if only the device embeds a tag, then this might mean that the device first needs to be extracted from the sterilized container prior to be activated when it might have already been determined that this is not the right endoscope to be used for a given medical act (without taking the device from the sterilized container).

Having device information at both the container and device level also allows for the activation software to track which container was activated and for what specific endoscope device. This is particularly useful for use-cases where the endoscope or part of the endoscope are return back to the manufacture using the original container, for example, in case certain parts of the endoscope device could be recycled or in case biopsy samples are captured within parts of the endoscope and need further lab analysis. Finally, by using 2 levels of tags, we can verify that the container's tag corresponds to a type of endoscope that is suitable for a given container. Toward this goal, the tag 101 can be associated with the container 100, the endoscope 102, or that there can be one tag for each of the container 100 and the endoscope 102.

The endoscope solution of FIG. 1 also preferably includes a provisioning and/or authorization software 200 that comprises at least one of a device communication API 201, a cloud communication API 202, a link to visualization software 203, and a local activation database replica 204.

During Manufacturing:

During manufacturing, provisioning software 200 is used to provision an endoscope with a serial number and/or product ID. The product ID identifies a class of devices (e.g., an endoscope optimized for biopsy sampling in urology versus or endoscope with only imaging capabilities used for other medical procedures). The serial number singles out a unit within an endoscope category. The provisioning software 200 itself is associated with a serial number or some form of unique identification. Provisioning can be done at the same time the endoscope's firmware is programmed.

Figure 2:
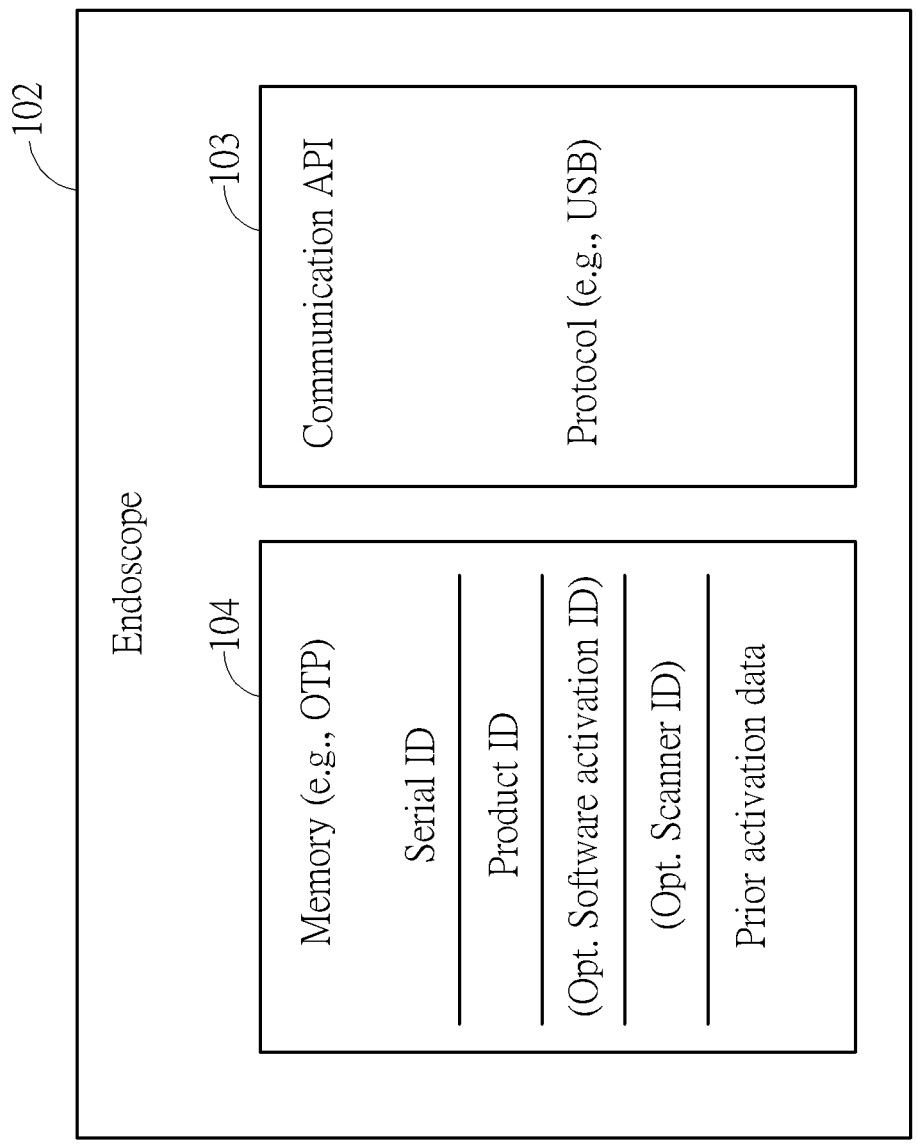
FIG. 2 is a schematic diagram showing example fields and information in the non-volatile memory of an endoscope device.

When an un-provisioned endoscope is first connected to the provisioning software 200 (for example, via USB), device communication API 201, communicating with communication API 103 can be used to inject the product ID and serial number to an endoscope's internal memory 104. The provisioning software 200 initializes the serial number and set a flag indicating that the device was never used. One example format of the product ID and serial number injected to an endoscope's internal memory is shown in FIG. 2, which illustrates an endoscope 102 having an internal memory 104 configured to contain the injected serial number, product ID, and prior activation data. Optionally, the memory 104 may be further configured to comprise a specific software activation ID and/or a scanner ID to be used before endoscope use. Provisioning software 200 may be assigned to one or more manufacturing entities.

During the endoscope device packaging step, tag 101 can also be used for identification (ID) and/or validation of disposable portions of the endoscope 102, such as a disposable cannula 105 or the entire endoscope in case 102 is fully disposable solution. Any appropriate form of identification can be used, for example inter alia, a bar code, a QR code, an alphanumeric code, and/or information transmitted by a wireless transceiver such as an RFID or NFC chip associated with the tag 101. In some embodiments, the tag 101 may be one single alphanumeric carrying a serial number that can only exist for a given product ID. As mentioned, the tag 101 can also be attached directly onto the endoscope device 102, to the container 100, or one tag 101 attached directly to each of the device 102 and the container 100 according to design considerations. In some embodiments, a tag 101 attached directly to the device 102 may contain different information than the tag 101 attached to the container 100.

During the programming of device information for the device and/or a device container, a database can be updated with serial number that have been assigned to alongside information regarding batch number and other information associated with the manufacturing context. In some embodiments, during programming the device information may be tied to a blockchain regarding activation and utilization of software applications and databases. For example, a particular service, discount, or other benefits may be available once the endoscope has been properly activated.

Authorizing a Pre-Provisioned Device or Container:

Once the provisioning software has provisioned an endoscope, an endoscope can then be used for an exam. For that, the endoscope is typically connected to a viewing system running a viewing software in a given medical facility (hospital, small medical offices, ambulances, etc . . . ). The viewing software can run an activation software component intended to ensure the authenticity of the endoscope and its adequate use for a given medical procedure.

The authorization software that is connected to endoscope apparatus 102 preferably further includes an activation database 300, which may be in the non-volatile memory 204 or may be located on another device, a remote server as an example. The activation database 300 may comprise fields or information about, inter alia, software ID 301, product ID, serial number (per software ID and product ID) 303, and a hash algorithm 304. The hash algorithm 304 may be applied to any of the fields or information to increase security and/or expedite database 300 searches.

If the endoscope is pre-provisioned with a product ID, the activation software will reject any tag number that would not satisfy some constraint on the serial number formatting. The serial number and product ID could also be dependent on the firmware revision. The serial number can also convey a maximum activation date.

The activation database may also reflect on the need to not-authorize a given set of endoscopes based on the need to recall a certain defective batch or other safety or regulatory reasons.

The information contained in the device or container can also be used by the viewing software to confirm that a given endoscope to be used offer the right hardware characteristics for a given exam. For example, a given product ID may correspond to a specific resolution or overall mechanical size of a given endoscope device implementation. When launching the viewer software, a given type of exam may be input. If the type of exam to be performed is not aligned with a set of valid product ID, the authorization software may reject the activation of a given endoscope.

At regular time intervals, the activation software 200 updates back the cloud database 300 to reflect the serial numbers and product IDs that were provisioned or scanned (from a tag 101 or by using the information contained into the internal memory 104). During software authorization, the cloud database 300 is queried for relevant information when the cloud database 300 is accessible. However, in some situations, for example in an ambulance, the cloud database 300 may be temporarily inaccessible. When the cloud database 300 is temporarily inaccessible, authorization information may be noted using the local activation database replica 204. Changes to the local activation database replica 204 while the cloud database 300 is temporarily inaccessible are synchronized to the cloud database 300 when the cloud database 300 becomes accessible again.

The activation software 200 optionally further includes a container or endoscope device tag-provisioning scanner 400. The optional scanner 400 may include a device communication API 401 and/or an activation software communication API 402. The scanner can be used to scan a tag 101 attached onto a container or the endoscope device to validate the device characteristic in the same way it is done with the information stored in the device memory In one embodiment of the optional scanner, the imaging front-end of the disposable endoscope 102 can be set to act as a scanner (e.g., the endoscope is used to scan a visual tag from the container).

Activation of the endoscope is detected and traced using sensors or wireless intercommunication devices so that when the endoscope is found to be unsuitable for a given medical act, a disablement means disables the endoscope in a mechanical or electrical way to ensure compliance with operating limits.

For example, the validation software 200 determines the endoscope 102 is invalid for any reason, it is preferred that the validation software 200 activates a disablement means that prevents usage of the invalid endoscope 102. Such disablement means are detailed in co-pending U.S. patent application Ser. No. 15/901,907 included herein by reference and may be used individually or in any combination. An electrical or software means is enacted to disable a cannula or an entire disposable endoscope, preventing the image sensor from sending any images or sequence of images to the handle. Warning signals may be issued. An electric current may be transmitted from the handle to the cannula to destroy electrically the cannula by burning the fuse, if any, of the cannula or any critical components within the cannula. The connection between the 'used' cannula and the handle may be blocked, either mechanically or electrically, so that an 'used' or invalid cannula will not be able to be mounted to the handle. Certain electro-mechanical contacts within the cannula or endoscope 102 via the proximity detection of the cannula using an RFID transceiver, an NFC transceiver, or an RFC antenna may be blocked. Electrically triggered magnets may also be used between the cannula and the handle to shutter-off or repulse electronic or mechanical connections.

In one embodiment of the authorization software, once an endoscope is used or removed from its sealed container, authorization software 200 can update the endoscope memory 104 to reflect on activation information and provide that information back to the cloud database 300 (intended use, viewer ID, container ID, etc . . . ). This enables full traceability throughout the device's lifetime.

Figure 3:
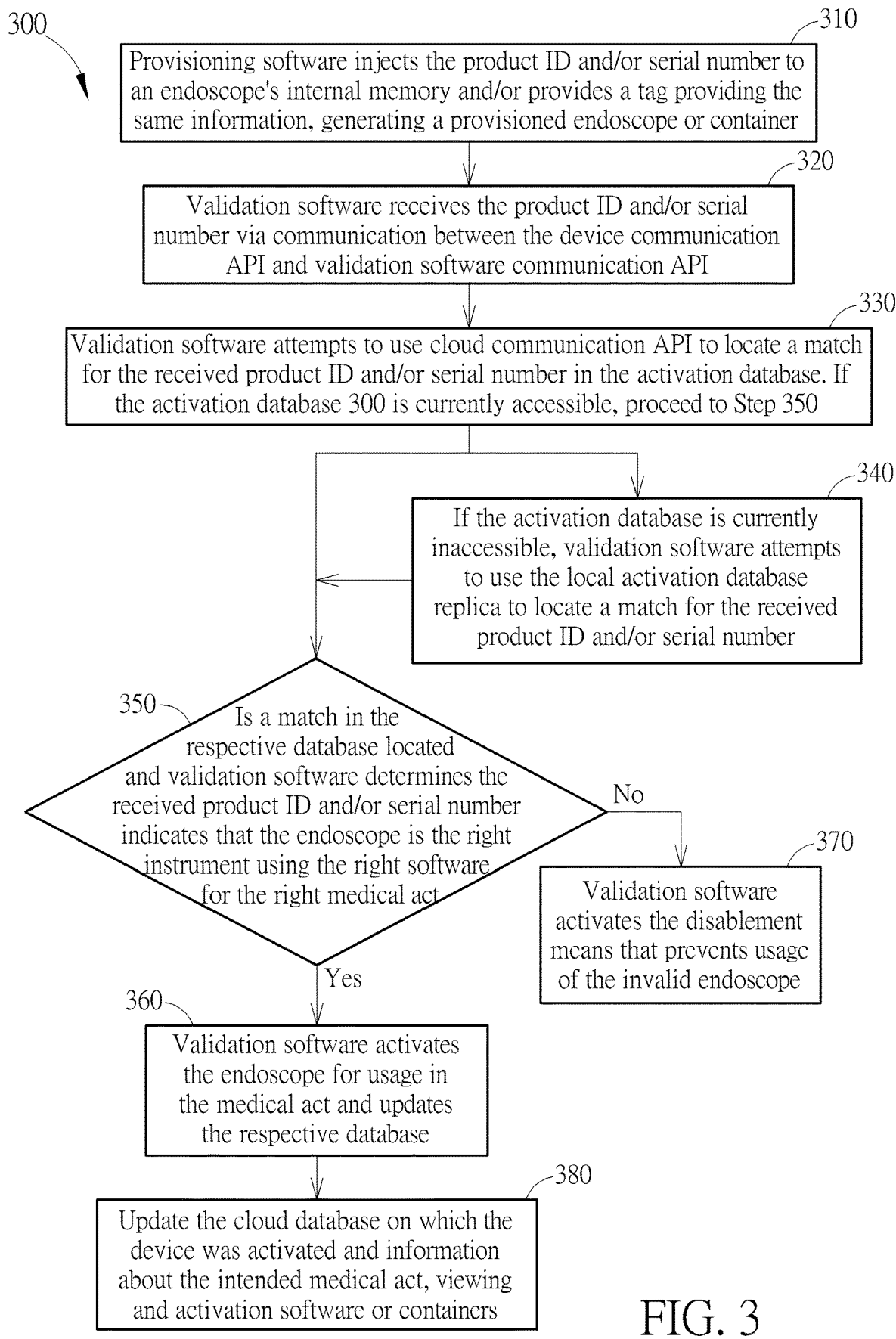
FIG. 3 is a flow chart 300 of use of the endoscope apparatus 1 according to an embodiment of the invention.

Preferred usage of the endoscope system 1 will now be described with reference to FIG. 3.

Step 310: Provisioning software injects the product ID and/or serial number to an endoscope's internal memory and/or provides a tag providing the same information, generating a provisioned endoscope or container.

Step 320: Validation software receives the product ID and/or serial number via communication between the device communication API and validation software communication API.

Step 330: Validation software attempts to use cloud communication API to locate a match for the received product ID and/or serial number in the activation database. If the activation database 300 is currently accessible, proceed to Step 350.

Step 340: If the activation database is currently inaccessible, validation software attempts to use the local activation database replica to locate a match for the received product ID and/or serial number.

Step 350: Is a match in the respective database located and validation software determines the received product ID and/or serial number indicates that the endoscope is the right instrument using the right software for the right medical act.

Step 360: Validation software activates the endoscope for usage in the medical act and updates the respective database. Go to step 380.

Step 370: Validation software activates the disablement means that prevents usage of the invalid endoscope. End.

Step 380: Update the cloud database on which the device was activated and information about the intended medical act, viewing and activation software or containers. End.

The endoscope apparatus provided in the invention has forced disposability of an invalid endoscope by the means and techniques put in described herein. Forced disposability ensures full traceability of the endoscope and guarantee that endoscope parts in contact with organic tissues or extracted from concealed containers cannot be re-used or if re-used, are used only in a way that aligns with their operating limits.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An endoscope apparatus capable of ensuring safe and compliant use, the endoscope apparatus comprising:
   an endoscope;
   a means for identification of the endoscope;
   a means for determining whether the endoscope is suitable for a given medical act utilizing the identification of the endoscope;
   a disablement means that prevents utilization of the endoscope when determined the endoscope is not suitable for the given medical act; and
   a cloud stored activation database comprising fields or information about software, product ID, and serial number utilized for determining whether the endoscope or a container of endoscope is suitable for a given medical act utilizing the at least one of a product ID and a serial number.

2. The endoscope apparatus of claim 1, wherein the means for identification of the endoscope comprises a tag fixed to the endoscope, the tag comprising at least one of a product ID or a serial number.

3. The endoscope apparatus of claim 1, further comprising a container encompassing the endoscope and the means for identification of the endoscope comprises a tag fixed to the container encompassing endoscope, the tag comprising at least one of a product ID or a serial number.

4. The endoscope apparatus of claim 1, wherein the endoscope comprises an internal non-volatile memory and the means for identification of the endoscope comprises the internal non-volatile memory comprising at least one of a product ID or a serial number.

5. The endoscope apparatus of claim 4, further comprising a container encompassing the endoscope and the means for identification of the endoscope comprises a tag fixed to the container encompassing endoscope, the tag comprising at least one of a product ID or a serial number.

6. The endoscope apparatus of claim 1, further comprising means for authorizing the use of the endoscope when determined the endoscope is suitable for a given medical act.

7. The endoscope apparatus of claim 6, further comprising a device provisioning scanner utilized for scanning a tag attached to the endoscope or attached to a container for the endoscope and inputting the at least one of a product ID and a serial number comprised by the tag into the means for determining whether the endoscope is suitable for a given medical act utilizing the identification of the endoscope.

8. The endoscope apparatus of claim 1, wherein the cloud stored activation database further comprises a hash algorithm applied to the fields or information to increase security and expedite activation database searches.

9. The endoscope apparatus of claim 1, further comprising a local activation database replica synchronized with the cloud stored activation database and utilized for determining whether the endoscope is suitable for a given medical act utilizing the at least one of a product ID and a serial number when the cloud stored activation database is inaccessible.

10. The endoscope apparatus of claim 1, further comprising updating the cloud database with information about which device was activated and information about the intended medical act, viewing and activation software, or containers used when determined the endoscope is suitable for the given medical act.

11. The endoscope apparatus of claim 1, wherein determining whether the endoscope is suitable for a given medical act includes at least one of whether a unit was previously used and should not be reused, expiration of the unit, recall of the unit, invalid authorization software license, improper unit for the given medical procedure, or invalid firmware version.

12. The endoscope apparatus of claim 1, wherein the disablement means includes at least one of preventing an image sensor from sending any images or sequences of images, transmitting an electric current to electrically burn a fuse or components, blocking a connection between a cannula and a handle, either mechanically or electrically, so that the cannula will not be able to be mounted to the handle, blockage of electro-mechanical contacts within the cannula or endoscope via proximity detection of the cannula using a Radio-frequency identification (RFID) transceiver, a Near Field Communication (NFC) transceiver, or Radio Frequency Choke (RFC) antenna, and electrically triggering magnets utilized between the cannula and the handle to shutter-off or repulse electronic or mechanical connections.

13. A method of ensuring compliant utilization of an endoscope, the method comprising:
provisioning an endoscope with a means for identification of the endoscope;
determining whether the endoscope is suitable for a given medical act utilizing the identification of the endoscope, wherein the determining includes accessing a cloud stored activation database comprising fields or information about software, product ID, and serial number for determining whether the endoscope or a container of endoscope is suitable for the given medical act utilizing the at least one of a product ID and a serial number; and
disabling utilization of the endoscope when determined the endoscope is not suitable for the given medical act.

14. The method of claim 13, wherein the means for identification of the endoscope comprises a tag fixed to the endoscope or to a container encompassing the endoscope, the tag comprising at least one of a product ID or a serial number.

15. The method of claim 13, further comprising updating the cloud stored activation database with information about which device was activated and information about the intended medical act, viewing and activation software, or containers used when determined the endoscope is suitable for the given medical act.

16. The method of claim 13, wherein each of the endoscope and the container is provisioned with a tag, and the method further comprises matching the container tag with the endoscope tag to ensure the proper endoscope goes back into the proper container when sending the endoscope back after the endoscope and/or exam is authorized and completed.

17. The method of claim 13, further comprising utilizing the means of identification to update the cloud stored activation database at each stage of the distribution and/or return of the endoscope to provide complete traceability.

18. A method of ensuring compliant utilization of an endoscope, the method comprising:
identifying an intended type of medical exam;
determining a product ID and/or a serial number of an endoscope;
determining whether the endoscope is of a correct class of endoscopes for the intended type of medical exam utilizing the product ID and/or the serial number of the endoscope;
activating the endoscope for the intended type of medical exam when determined that the endoscope is of the correct class for the intended type of medical exam; and
disabling the endoscope when determined the endoscope is not of the correct class for the intended type of medical exam.

19. The method of ensuring compliant utilization of an endoscope of claim 18, further comprising determining whether the endoscope is of the correct class for the intended type of medical exam utilizing the product ID and/or the serial number of the endoscope includes searching a database for a matching serial number and/or product ID and activating the endoscope when a match is found that indicates the endoscope is of the correct class for the intended type of medical exam and disabling the endoscope when no match is found that indicates the endoscope is of the correct class for the intended type of medical exam.

20. The method of ensuring compliant utilization of an endoscope of claim 19, wherein the database is a cloud stored activation database comprising fields or information about software, product ID, and serial number utilized for determining whether the endoscope or a container of endoscope is the endoscope is of the correct class for the intended type of medical exam.

21. The method of ensuring compliant utilization of an endoscope of claim 18, further comprising provisioning the endoscope, wherein provisioning the endoscope comprises fixing a tag to the endoscope with the tag comprising at least one of the product ID or the serial number, fixing a tag comprising at least one of the product ID or the serial number to a container encompassing the endoscope, and/or storing at least one of the product ID or the serial number to an internal non-volatile memory of the endoscope.

* * * * *